United States Patent [19]
Ivester et al.

[11] Patent Number: 5,209,761
[45] Date of Patent: May 11, 1993

[54] LIQUID TRAP WITH PURGE PORT

[75] Inventors: Paul A. Ivester, Seattle; Jeffrey M. Payne, Snohomish, both of Wash.

[73] Assignee: SpaceLabs Medical, Inc., Redmond, Wash.

[21] Appl. No.: 894,057

[22] Filed: Jun. 3, 1992

[51] Int. Cl.$^5$ .............................................. B01D 45/12
[52] U.S. Cl. ........................................... 55/21; 55/169; 55/189; 55/213; 55/270; 128/719; 128/730
[58] Field of Search .................. 55/164, 189, 204, 218, 55/219, 270, 459.1, DIG. 35, 21, 213, 55; 128/205.27, 719, 730

[56] References Cited

U.S. PATENT DOCUMENTS

| | | | |
|---|---|---|---|
| 4,274,425 | 6/1981 | Lutz et al. | 128/719 |
| 4,535,820 | 8/1985 | Raines | 137/854 |
| 4,592,368 | 6/1986 | Ricciardelli et al. | 128/719 |
| 4,713,095 | 12/1987 | Ricciardelli | 55/189 |
| 4,717,403 | 1/1988 | Choksi | 55/DIG. 35 X |
| 4,821,737 | 4/1989 | Nelson | 128/730 |
| 5,096,598 | 3/1992 | Pecen et al. | 55/218 X |

*Primary Examiner*—Charles Hart
*Attorney, Agent, or Firm*—Seed and Berry

[57] ABSTRACT

A liquid trap for removing liquid such as condensed water vapor from gas in a patient's sampled airstream. The liquid trap includes a separation chamber that is used to separate the liquid from the gas. An opening in the separation chamber allows the liquid to flow into a collection chamber where it is temporarily stored. The collection chamber has a purge port that allows the chamber to be emptied of liquid without removing the chamber from a gas analyzer. A check valve is coupled to the purge port to retain the liquid in the collection chamber. Electrodes sense when the liquid reaches a predetermined level. A vacuum is applied to the check valve to remove the liquid from the collection chamber through the purge port.

9 Claims, 1 Drawing Sheet

LIQUID TRAP WITH PURGE PORT

DESCRIPTION

1. Technical Field

The present invention relates to the measurement of gases such as carbon dioxide in the exhaled breath of a patient. More particularly, the present invention relates to liquid traps used to remove and collect liquid from the patient's breath.

2. Background of the Invention

The measurement of a patient's carbon dioxide level (known as capnography) is an important parameter in the diagnosis of a patient's pulmonary function. Capnography is done on a continuous basis and the values of carbon dioxide level are displayed as a curve on a CRT.

Measurement of carbon dioxide gas level is done by aspirating a continuous stream of gas from the patient's exhalation line and feeding it into an infrared sensor. The flow rate of the sample stream is usually 200 ml/min or less. In order to minimize dampening of the signal, the internal volume of the sampling line is kept as small as possible (about 2 ml). The inside diameter of the sampling line is often 1 mm (0.40 inches) or smaller.

The exhaled gases leave the patient at approximately 99° Fahrenheit (F) and virtually 100 percent relative humidity. The gas cools in the sampling line (the line is at room temperature usually around 70°) and moisture condenses. If the condensed moisture is drawn into the gas sensor, it can cause malfunction. Therefore, it is important to remove this moisture from the line and collect it in container for easy disposal.

Prior art devices, such as that disclosed in U.S. Pat. No. 4,717,403, have employed a liquid trap to remove and collect condensed moisture. With these devices, when the liquid trap fills with condensed moisture the trap is removed and discarded, and a new trap is used. Alternatively, the bottom of the trap that contains the condensed moisture is removed and the water is dumped from the bottom. The bottom is then replaced on the trap. One disadvantage of this approach is that the water trap and downstream capnography equipment are unusable during the period that the bottom of the trap is removed. On patients being tested for only a short period of time, or on patients having relatively low humidity levels, the discarding and replacing requirement may not be overly onerous. However, many patients are monitored for extended periods of time, requiring repeated replacement of the liquid traps. In addition, in some situations additional humidity is administered to the patient. This requires prior art liquid traps to be replaced as often as every 1-2 hours.

SUMMARY OF THE INVENTION

The present invention is directed to a liquid trap for removing liquid from gas in a sampled airstream from a patient and temporarily collecting the liquid. The trap includes a moisture separating means for separating liquid from gas in a sampled airstream from a patient having a first opening for ingress of the sampled airstream from the patient, a second opening for egress of the gas after the liquid has been removed from the airstream, and a third opening for egress of the liquid. A collection chamber communicates with the third opening to receive the liquid from the moisture separation means. The collecting chamber has a purge port for removal of the liquid from the collection chamber when a predetermined amount of liquid has been collected in the collection chamber. In a preferred embodiment, a check valve covering the purge port prevents liquid from exiting the collection chamber until a pressure differential is applied to the check valve from the interior to the exterior of the collection chamber. The liquid trap may further include level detection means for detecting when the liquid within the collection chamber reaches a predetermined level.

DETAILED DESCRIPTION OF THE INVENTION

Figures 1, 2:
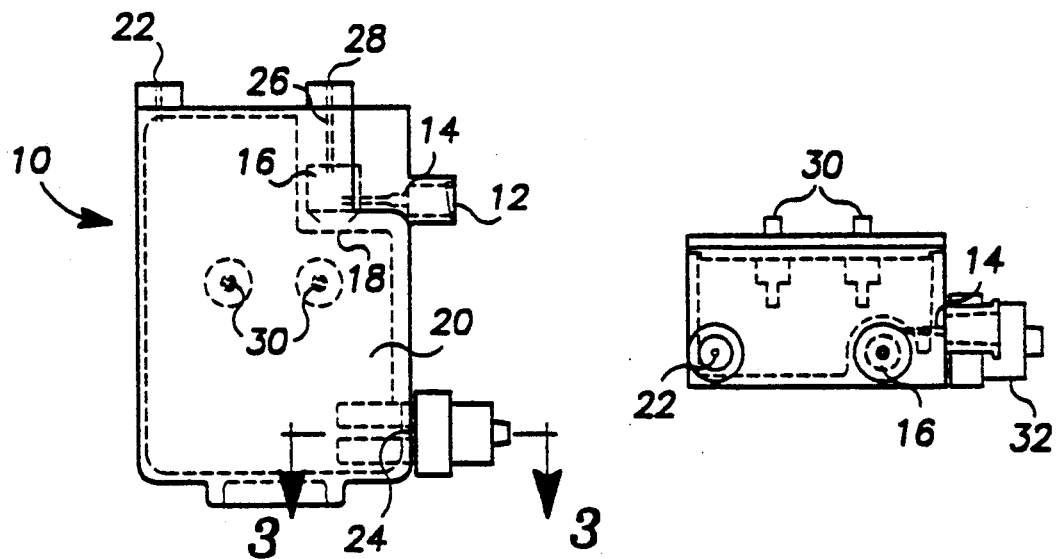
FIG. 1 is a side elevational view of the liquid trap of the present invention.
FIG. 2 is a top plan view of the liquid trap of FIG. 1.

The level of carbon dioxide in a patient's exhaled airstream is determined by conveying the airstream to a sample analyzer (not shown). However, a liquid trap of the present invention is placed in the airstream upstream from the analyzer to prevent excess moisture from reaching the analyzer. FIG. 1 shows one embodiment of a liquid trap 10 having an input opening 12 for receiving a sampled airstream from a patient. The airstream includes carbon dioxide and other gases as well as condensed moisture. The airstream is drawn through an input channel 14 into a separation chamber 16.

As shown in FIG. 2, the airstream enters the separation chamber 16 tangentially so that the airstream flows circularly within the separation chamber, causing a centrifugal separation of the gas and condensed moisture. Because the gas is lighter, it separates from the condensed moisture and exits the separation chamber through chamber output channel 26 as shown in FIG. 1. The gas exits the liquid trap through output port 28 which is connected to the sample analyzer. A vacuum (not shown) draws the gas through the separation chamber and through the sample analyzer. The moisture, being heavier, falls to the bottom of the separation chamber 16 and is pulled through a bottom hole 18 of the separation chamber due to gravity. The liquid drops into collection chamber 20 where it is temporarily stored. A vacuum is connected to an air vacuum port 22 communicating with the collection chamber so as to help draw the liquid through the bottom hole 18 in the separation chamber 16 and into the collection chamber 20.

In contrast to prior art liquid traps, the collection chamber includes an outlet or purge port 24. The purge port allows the collection chamber to be drained without removing the trap from the sample analyzer. The liquid exits the collection chamber through the purge port and is discarded. In a preferred embodiment, electrodes 30 are positioned within the collection chamber 20 so as to detect when the liquid reaches a predetermined level within the collection chamber. When the liquid reaches the predetermined level it closes a circuit that includes the electrodes. The electrodes can be connected to an alarm to alert personnel that the collection chamber should be emptied. Alternatively, the electrodes can be connected to a device that automatically empties the collection chamber.

In a preferred embodiment, a check valve 32 is coupled to the purge port 24 to selectively prevent liquid from flowing through the purge port 24. Although many types of check valves may be employed, the preferred check valve is described by U.S. Pat. No. 4,535,820, incorporated herein in its entirety. When it is desired to remove the liquid from the collection chamber, a vacuum may be applied to the check valve. This would typically be done with a syringe or a suction hose. This allows the trap to be emptied without removing it from the analyzer.

The use of a pressure sensitive check valve has several advantages over other types of closure means for the purge port 24. First, a vacuum that would be needed to draw water from the collection chamber 20 (since the collection chamber is maintained at reduced pressure) also automatically opens the valve 32. If another type of closure means (such as a plug) was used, it would first be necessary to open the closure means prior to withdrawing the water.

Second, the use of a vacuum to open the check valve 32 has no adverse effect on the operation of either the liquid trap 10 or the downstream capnography equipment. This properly occurs because the interior of the collection chamber 20 is already at reduced pressure during normal operation. As a result, it is not necessary to suspend use of the trap 10 or capnography equipment when the collection chamber 20 is being emptied.

Figure 3:
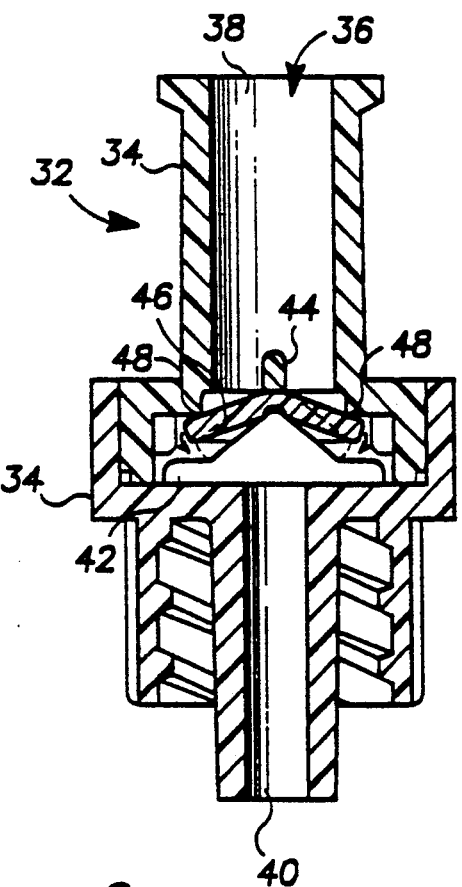
FIG. 3 is a cross-sectional view of a check valve used with the liquid trap of the present invention.

Referring now to FIG. 3, the check valve 32 includes a body member 34 having an internal chamber 36. Chamber 36 has an input opening 38 that communicates with the purge port 24. Chamber 36 also has an output opening 40 that communicates with the input opening 38 and the purge port 24 when the check valve is open. This allows liquid to be drained from the purge port through the open check valve and out of the output opening. Positioned within the chamber 38 is a triangular pointed member 42 affixed to the interior of the body member 34. The pointed member 42 is positioned transversely across the chamber 36 but has a width smaller than the diameter of the chamber to allow the free flow of liquid from the input opening 38 to the output opening 40 when the valve is open. Positioned above the pointed member 42 is a traverse cross bar 44 affixed to the interior of the body member 34. Positioned between the traverse cross bar 44 and the pointed member 42 is a resilient valve disk 46. The periphery of the valve disk 46 contacts a shoulder portion 48 of the chamber 36 to form a seal to prevent liquid from flowing from the input opening 38 to the output opening 40.

As long as the pressure inside the collection chamber 20 does not exceed the pressure of the atmosphere, the check valve 32 remains closed because of the valve disk 46 sealing against the shoulder 48 of the valve chamber 36. In normal operation there is a slight vacuum inside the collection chamber caused by the vacuum source connected to the air vacuum port 22. This vacuum helps to ensure that the valve disk remains sealed against the shoulder.

When it is desired to drain the liquid from the collection chamber, a vacuum source is applied at the output opening 40 of the check valve chamber 36. Instead of a vacuum on the check valve, a positive pressure could be exerted on the liquid to force it out of the check valve. The vacuum or positive pressure causes the valve disk to flex downward as shown by the arrows in FIG. 3. This downward flexing removes the sealing contact between the valve disk 46 and the shoulder 48. This allows the liquid to flow between the valve disk and the shoulder portion, by the triangular pointed member 42 and out of the valve chamber 36 through output opening 40.

As will be appreciated by those skilled in the art, check valve 32 is merely a preferred embodiment of the present invention. The check valve may be any pressure sensitive valve that allows the collection chamber 20 to fill during normal operation, while allowing the collection chamber to be drained by the application of a vacuum on the check valve. Alternatively, the check valve may be removed entirely and replaced by a removable cap or plug.

From the foregoing it will be appreciated that, although specific embodiments of the invention have been described herein for purposes of illustration; various modifications may be made without deviating from the spirit and scope of the invention. Accordingly, the invention is not limited except as by the appended claims.

We claim:

1. A liquid trap for removing liquid from gas in a sampled airstream from a patient and temporarily collecting the liquid, comprising:
   a moisture separating means for separating liquid from gas in a sampled airstream from a patient, said moisture separating means having a first opening for ingress of the sampled airstream from the patient, a second opening for egress of gas after the liquid has been removed from the airstream, and a third opening for egress of the liquid;
   a collection chamber communicating with the third opening to receive the liquid from the moisture separation means;
   a purge port communicating with the interior of said collection chamber for removal of the liquid from the collection chamber when a predetermined amount of liquid has been collected in the collection chamber; and
   a check valve coupled to the purge port for preventing liquid from exiting the collection chamber until a negative pressure differential is applied to the check valve to draw the liquid out through the purge port.

2. The liquid trap of claim 1 wherein the check valve includes a body having an interior chamber extending from a first opening in communication with the purge port to a second opening, the chamber having a shoulder, the check valve further including a resilient valve disk positioned within the chamber and a pointed member supporting the valve disk at its center, the pointed member also forcing the valve disk into contact with the shoulder of the chamber to prevent liquid from flowing from the first opening to the second opening until a pressure above a predetermined amount is exerted on the liquid tending to force the valve disk away from the shoulder portion to allow the liquid to flow from the first opening to the second opening.

3. The liquid trap of claim 1 wherein the collection chamber includes an air vacuum port positioned above the liquid such that a vacuum applied to the air vacuum port tends to pull the liquid away from the purge port.

4. The liquid trap of claim 1, further comprising level detection means for detecting when the liquid within the collection chamber reaches a predetermined level.

5. A liquid trap for removing liquid from gas in a sampled airstream from a patient and temporarily collecting the liquid, comprising:
   a moisture separating means for separating liquid from gas in a sampled airstream from a patient, having a first opening for ingress of the sampled airstream from the patient, a second opening for egress of gas after liquid has been removed from the airstream, and a third opening for egress of the liquid;

a collection chamber communicating with the third opening to receive the liquid from the moisture separation means, the collecting chamber having a purge port for removal of the liquid from the collection chamber when a predetermined amount of liquid has been collected in the collection chamber;

an air vacuum port positioned in the collection chamber above the liquid such that a vacuum applied to the air vacuum port tends to pull the liquid away from the purge port; and a check valve coupled to the purge port such that the liquid is prevented from exiting the collection chamber until a vacuum is applied to the exterior of the check valve to draw the liquid out through the purge port.

6. The liquid trap of claim 5, further comprising level detection means for detecting when the liquid within the collection chamber reaches a predetermined level.

7. The liquid trap of claim 5 wherein the check valve includes a body having an interior chamber extending from a first opening in communication with the purge port to a second opening, the chamber having a shoulder, the check valve further including a resilient valve disk positioned within the chamber and a pointed member supporting the valve disk at its center, the pointed member also forcing the valve disk into contact with the shoulder of the chamber to prevent liquid from flowing from the first opening to the second opening until a pressure above a predetermined amount is exerted on the liquid tending to force the valve disk away from the shoulder portion to allow the liquid to flow from the first opening to the second opening.

8. In a liquid trap for removing liquid from gas in a sampled airstream from a patient and temporarily collecting the liquid, a method comprising:

separating liquid from gas in a sampled airstream from a patient using a separation chamber;

transmitting continuously the liquid from the separation chamber to a collection chamber;

allowing the liquid to collect in the collection chamber;

periodically applying a pressure differential across an opening in the collection chamber with the pressure inside the collection chamber being greater than the pressure outside the collection chamber thereby drawing the liquid from the collection chamber through the opening.

9. The method of claim 8, wherein the applying a pressure differential step includes generating a vacuum from outside of the opening in the collection chamber to draw the liquid through the opening.

* * * * *